(12) United States Patent
Meadows et al.

(10) Patent No.: US 9,598,158 B2
(45) Date of Patent: Mar. 21, 2017

(54) OXYGEN TANK FLOTATION DEVICE (71) Applicants: Madison Victoria Meadows, Tacoma, WA (US); Sharon Marie Erickson, University Place, WA (US); Stephen Paul Erickson, Tacoma, WA (US)

(72) Inventors: Madison Victoria Meadows, Tacoma, WA (US); Sharon Marie Erickson, University Place, WA (US); Stephen Paul Erickson, Tacoma, WA (US)

( * ) Notice: Subject to any disclaimer, the term of this patent is extended or adjusted under 35 U.S.C. 154(b) by 70 days.

(21) Appl. No.: 14/832,677

(22) Filed: Aug. 21, 2015

(65) Prior Publication Data

US 2017/0050706 A1 Feb. 23, 2017

(51) Int. Cl.
| | |
|---|---|
| *B63B 35/00* | (2006.01) |
| *B63B 38/00* | (2006.01) |
| *B63C 11/20* | (2006.01) |
| *B63C 11/18* | (2006.01) |
| *B63C 11/02* | (2006.01) |

(52) U.S. Cl.
CPC ............... *B63C 11/20* (2013.01); *B63B 35/00* (2013.01); *B63B 38/00* (2013.01); *B63C 11/18* (2013.01); *A61M 2209/08* (2013.01); *B63C 2011/023* (2013.01); *B63C 2011/024* (2013.01)

(58) Field of Classification Search
CPC ....... B63B 35/00; B63B 35/58; B63B 35/607; B63B 38/00; B63C 9/00; B63C 9/04; B63C 9/08; B63C 11/02; B63C 2011/023; B63C 2011/024; B63C 2011/025; B63C 2011/026; B63C 11/18; B63C 11/20; B63C 11/202; B63C 11/205; B63C 11/207; A61G 1/00; A61G 1/044; A61M 2209/08

See application file for complete search history.

(56) References Cited

U.S. PATENT DOCUMENTS

| | | | | |
|---|---|---|---|---|
| 4,919,631 A * | 4/1990 | Stafford | ................ | B63C 11/202 114/315 |
| 5,299,721 A * | 4/1994 | Cummings | ............. | B60R 11/00 114/345 |
| 5,546,885 A * | 8/1996 | Porada | .................... | B63B 7/085 114/315 |
| 6,964,073 B1 * | 11/2005 | Curry | ....................... | A61G 1/00 128/870 |
| 8,328,592 B2 * | 12/2012 | Cynamon | ................ | A61G 1/01 441/40 |
| 9,187,160 B2 * | 11/2015 | McJunkin | ............... | B63C 11/18 |
| 2011/0185504 A1 * | 8/2011 | Kenalty | .................... | A61G 1/00 5/626 |
| 2015/0093201 A1 * | 4/2015 | Escano Cavanilles | ............ | B63C 11/202 405/194 |

* cited by examiner

*Primary Examiner* — Ajay Vasudeva (57) ABSTRACT

This flotation device for oxygen tanks is created to allow anyone dependent upon supplemental oxygen to utilize the pool or shallow water for recreation, exercise or therapy. Having their tank close to them in the pool or shallow waters, allows for more freedom of movement and safety for themselves and for others. The flotation device for oxygen tanks includes a base member flotation board with attachment members that include flotation tubes, straps, buckles and a grommet to secure the tank to the base member.

6 Claims, 14 Drawing Sheets

OXYGEN TANK FLOTATION DEVICE

CROSS REFERENCE TO RELATED APPLICATIONS

There is no cross reference to related applications.

STATEMENT REGARDING FEDERALLY SPONSORED RESEARCH OR DEVELOPMENT

Not applicable to this application.

BACKGROUND OF THE INVENTION

Medical type device designed for aquatic purpose(s) relating to small portable oxygen tanks used by people who are dependent upon supplemental oxygen.

BRIEF SUMMARY

This device allows people who are dependent on supplemental oxygen to be in a pool with their small portable oxygen tank kept securely close to them for the purpose of simple water therapy, medical aqua therapy, physical therapy, low impact water exercise, water walking and personal water recreation.

This device has not been anticipated, rendered obvious, suggested, or even implied by any other individual or company.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

WHAT IT IS NOT

It is not a life-saving flotation device or a toy. It is not for use in large bodies of deep water.

EXPLANATION

This device secures a small portable oxygen tank to a Base Member Flotation Board using additional Attachment Member Flotation Tubes and Attachment Member Straps with Attachment Member Buckles and a grommet, allowing the user easy access to the oxygen tank while keeping it securely close to them while they are in a pool or small body of water. Oxygen tanks that have continuous-flow regulators are approved to get wet.

I. Base Member Flotation Board

Figure 2:
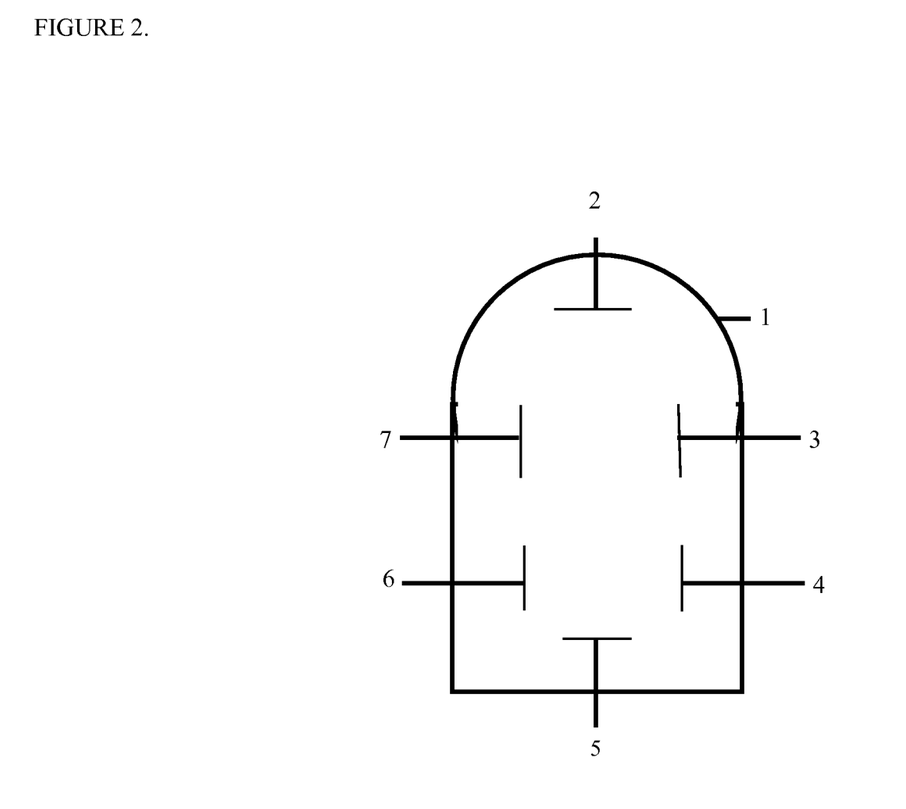
FIG. 2 on Sheet 2 of 14, is the front perspective view of the Base Member Flotation Board (1) with slits (2, 3, 4, 5, 6, 7) for Prototype A.
Figure 3:
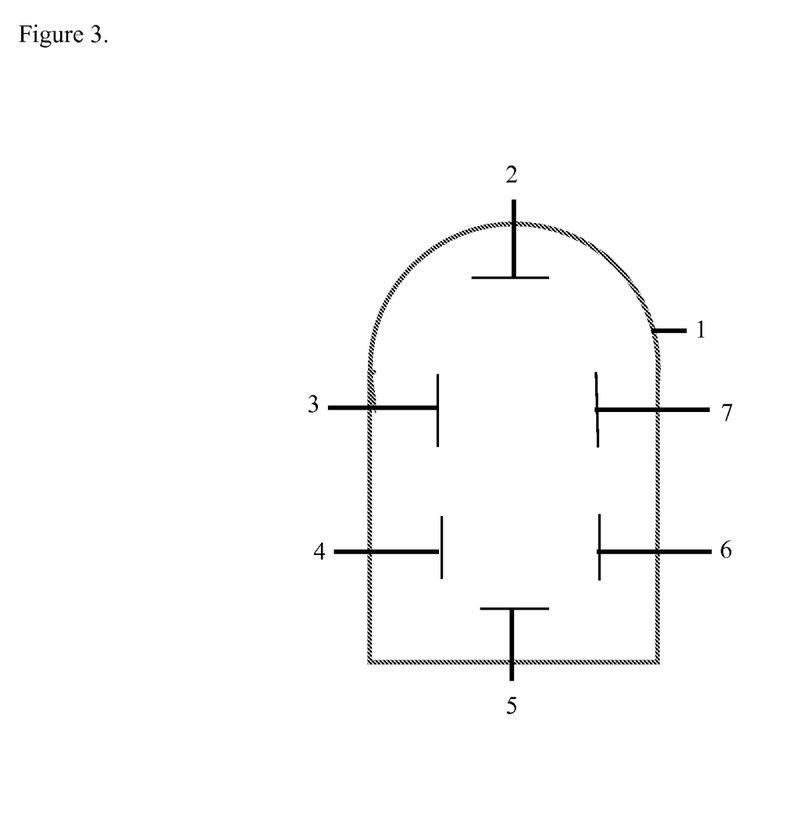
FIG. 3 on Sheet 3 of 14, is the back perspective of the Base Member Flotation Board (1) with slits (2, 3, 4, 5, 6, 7) for Prototype A.

The Base Member Flotation Board (1) indicated in Prototype A, FIG. 2 and FIG. 3 on Sheet 2 of 14 and on sheet 3 of 14 is a board made of high density closed-cell EVA foam that measures 17 inches long from the top of the top middle of the board (1) to the bottom. The width of the Base Member Flotation Board (1) is 12 inches. The Base Member Flotation Board (1) may be named either the base member or board in all drawings and explanations. The depth of the board (1) is 1¼ inches. All slits are 1⅝ inches long and ⅜ inches wide and continue completely through the 1¼ inches of board (1). Slit (2) on FIG. 2 is 1 inch down from the top of the board (1) and centered extending 1⅝ inches in length with an opening of ⅜ inch and goes through the 1¼ inches of board (1). Slit (3) is 3 inches from the right side of the board (1) and begins 5 inches from the end of slit (4), drawn straight up for 1⅝ inches. Slit (4) is 3 inches from the right side of the board (1) and begins 3½ inches from the bottom of the board (1) drawing straight up for 1⅝ inches with a width of ⅜ inch and the slit goes through the 1¼ inches of board (1). Slit (5) is 1½ inches from the bottom of the board (1) and is centered extending 1⅝ inches with a width of ⅜ inch, the slit going through the 1¼ inches of board (1). Slit (6) is 3 inches from the left side of the board (1) and begins 3½ inches from the bottom of the board drawing straight up for 1⅝ inches with a width of ⅜ inch and goes through the 1¼ inches of board (1). Slit (7) is 3 inches from the left side of the board (1) and begins 5 inches from the top of slit (6) of the board (1) drawing straight up for 1⅝ inches with a width of ⅜ inch and goes through the 1¼ inches of board (1).

The Base Member Flotation Board (1) could be made of different types of foam such as closed-cell foams including but not limited to the following: Polyethylene, Cross linked Polyethylene, Polystyrene, Neoprene rubber, Gym rubber, and Polypropylene foam or styrofoam.

The size of the board (1) could be a length of 16 inches up to 30 inches and a width of 9 inches up to 20 inches. The depth of the board (1) could be from 1 inch to 3 inches. The board could be square, rectangular, triangular, circular, diamond shape, or oval. There could be a curve of any angle from 182 degrees through 190 degrees. The board (1) could also have no curve or could have a triangular shape of any angle. All slits could be from one inch through 3 inches in length and could be from ¼ through one inch wide. The slits could be situated anywhere on the board.

Base Member of Prototype B.

Figure 11:
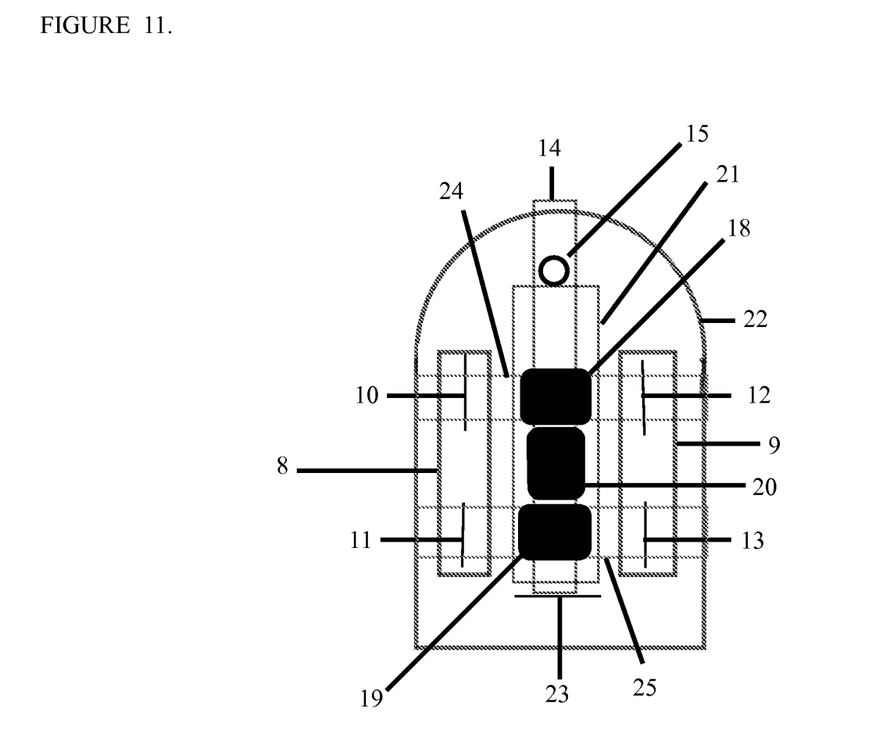
FIG. 11 on Sheet 7 of 14 is an upper perspective view of Prototype B.
Figure 12:
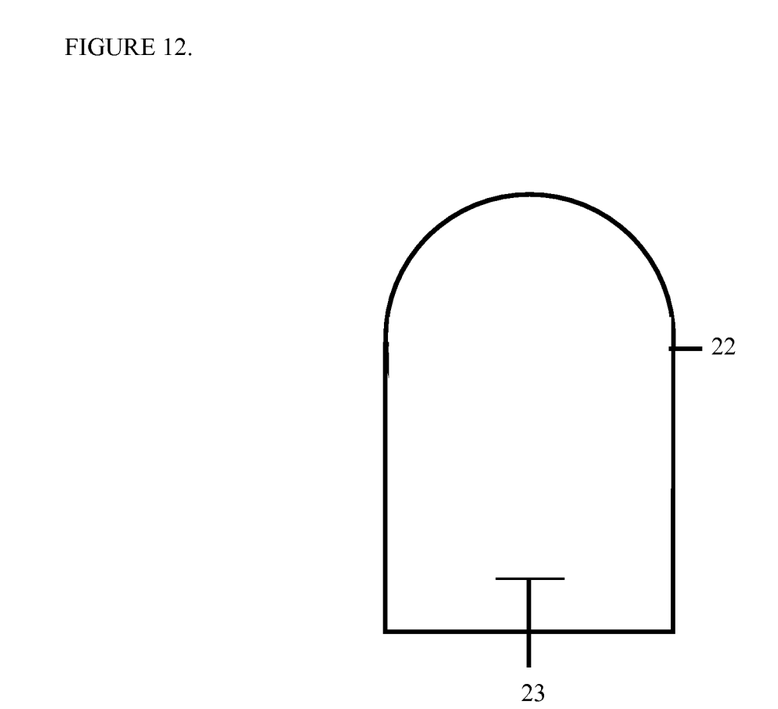
FIG. 12 on Sheet 8 of 14 is the front perspective view of the Base Member Flotation Board Prototype B (22) which only has one slit (23) that is located at the bottom of the Base Member Flotation Board (22).

The base member indicated in Prototype B (FIG. 11 on Sheet 7 and FIG. 12 on Sheet 8 of 14) is a board (22) made of high density closed-cell EVA foam that measures 17 inches long from the top of the middle of the top of the board to the bottom. Prototype B Board (22) has a 12 inch width. The base member (22) may be named either the base member or board in all drawings and explanations. The depth of the board (22) is 1¼ inches. All slits are 1⅝ inches long and ⅜ inches wide and continue completely through the 1¼ inches of board (22). Slit (23) pictured in FIG. 11 on Sheet 7 and FIG. 12 on Sheet 8 of 14 is 3½ inches from the bottom of the board, centered, drawing horizontal for 1⅝ inches with a width of ⅜ inch and the slit (23) goes through the 1¼ inches of the board (22).

The size of the board (22) could be a length of 16 inches up to 30 inches and a width of 9 inches up to 20 inches. The depth of the board (22) could be from 1 inch to 3 inches in depth. The curve could be any angle from 182 degrees through 190 degrees. The board (22) could also have no curve or could have a triangular shape of any angle. The board (22) could be square, rectangular, triangular, circular, diamond shape, or oval.

The base member (22) could be made of different types of foam such as closed-cell foams including but not limited to the following: Polyethylene; Cross linked Polyethylene; Polystyrene; Neoprene rubber; Gym rubber; and Polypropylene foam styrofoam.

Base Member of Prototype C.

Figure 17:
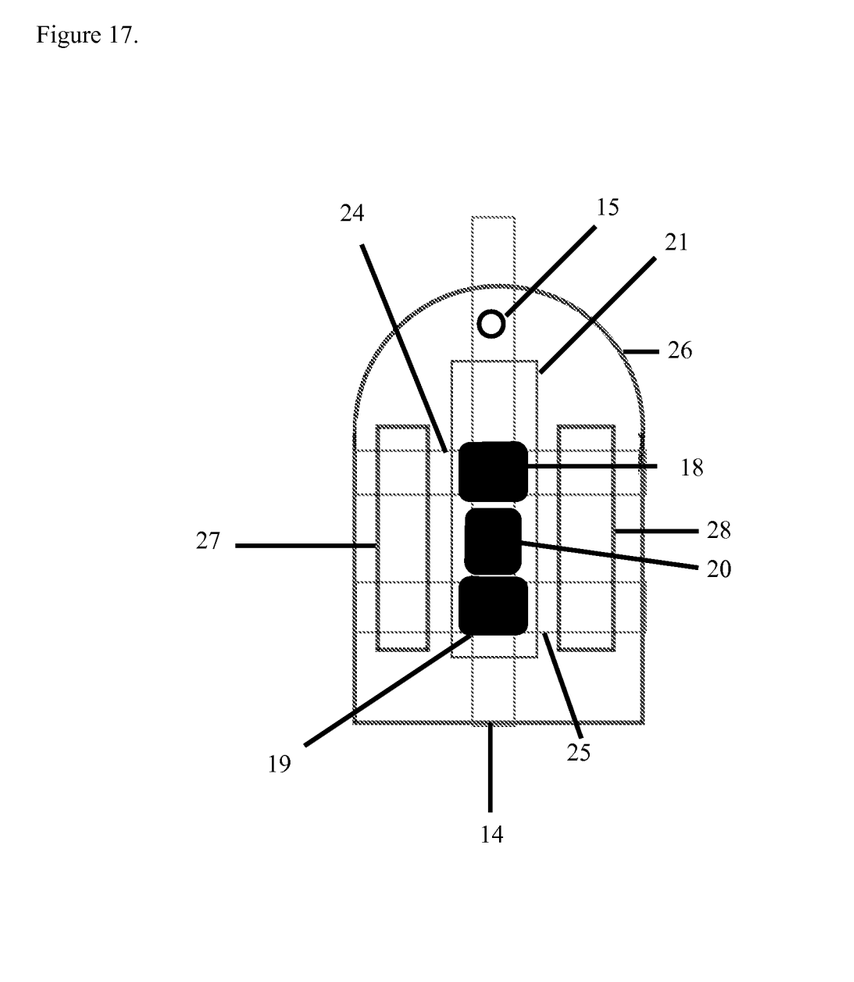
FIG. 17 on Sheet 11 of 14 is an upper perspective view of Prototype C.
Figure 18:
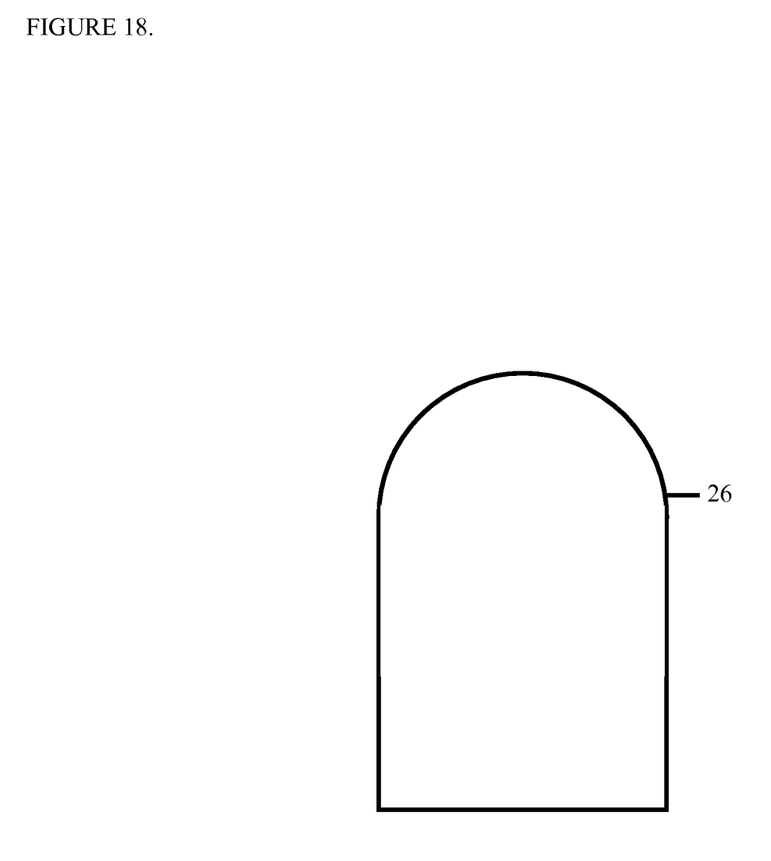
FIG. 18 on Sheet 12 of 14 is an upper view of Base Member Flotation Board for Prototype C (26), which is distinguished by having no slits in the Base Member Flotation Board (26).

The board (26) indicated in Prototype C, FIG. 17 on Sheet 11 of 14 and FIG. 18 on sheet 12 of 14 is a board (26) made of high density closed-cell EVA foam that measures 17 inches long from the top of the middle of the top of the board (26) to the bottom. The board (26) has a width of 12 inches. The base member (26) may be named either the base member or board in all drawings and explanations. The depth of the board (26) is 1¼ inches.

The size of the board (26) could be a length of 16 inches up to 30 inches and a width of 9 inches up to 20 inches. The depth of the board (26) could be from 1 inch to 3 inches. The curve could be any angle from 182 degrees through 190 degrees. The board (26) could also have no curve or could have a triangular shape of any angle. The board (26) could be square, rectangular, triangular, circular, diamond shape, or oval.

The base member (26) could be made of different types of foam such as closed-cell foams including but not limited to the following: Polyethylene, Cross linked Polyethylene, Polystyrene, Neoprene rubber, Gym rubber, and Polypropylene foam or styrofoam.

II. Attachment Member Flotation Tubes

Figure 1:
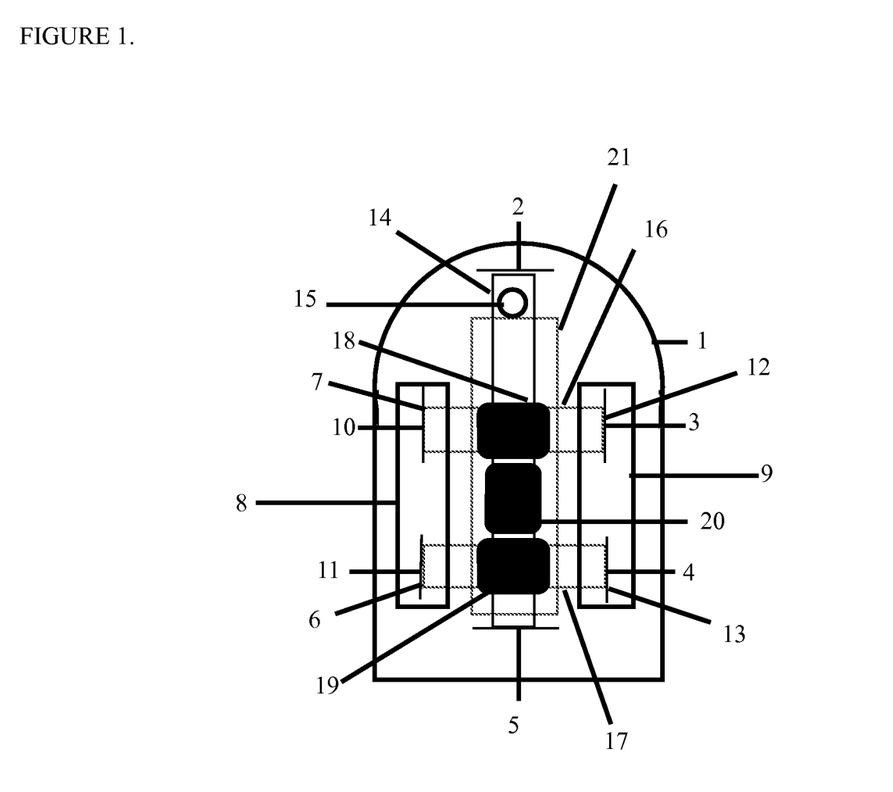
FIG. 1 on Sheet 1 of 14 is an upper perspective view of the present invention in use, Prototype A.
Figure 20:
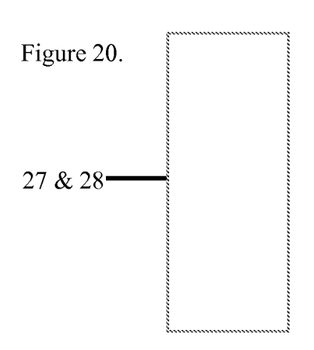
FIG. 20 on Sheet 14 of 14 is the upper view of the Attachment Member Tubes of Prototype C (27, 28).

See Attachment Member Flotation Tubes shown in Sheets 1 of 14, FIG. 1, (8, 9); Sheets 4 of 14, FIG. 4, (8, 9); Sheet 5 of 14, FIG. 5, (8, 9); Sheet 7 of 14, FIG. 11, (8, 9); Sheet 9 of 14, FIG. 13, (8, 9) and Sheet 10 of 14, FIG. 14, (8, 9) are all the same size with the same slits that are labeled 10 and 11 in tube 8, and 12 and 13 for tube 9. These tubes (8, 9) are the same in Prototypes A and B. Prototype C has no slits in the attachment member flotation tubes as seen in FIG. 20, Sheet 14 of 14, (27, 28). All Prototypes are the same size of 12 inches long and 3½ inches in diameter. The Attachment Member Flotation Tubes may be named either tube or tubes in all drawings and explanations.

Figure 4:
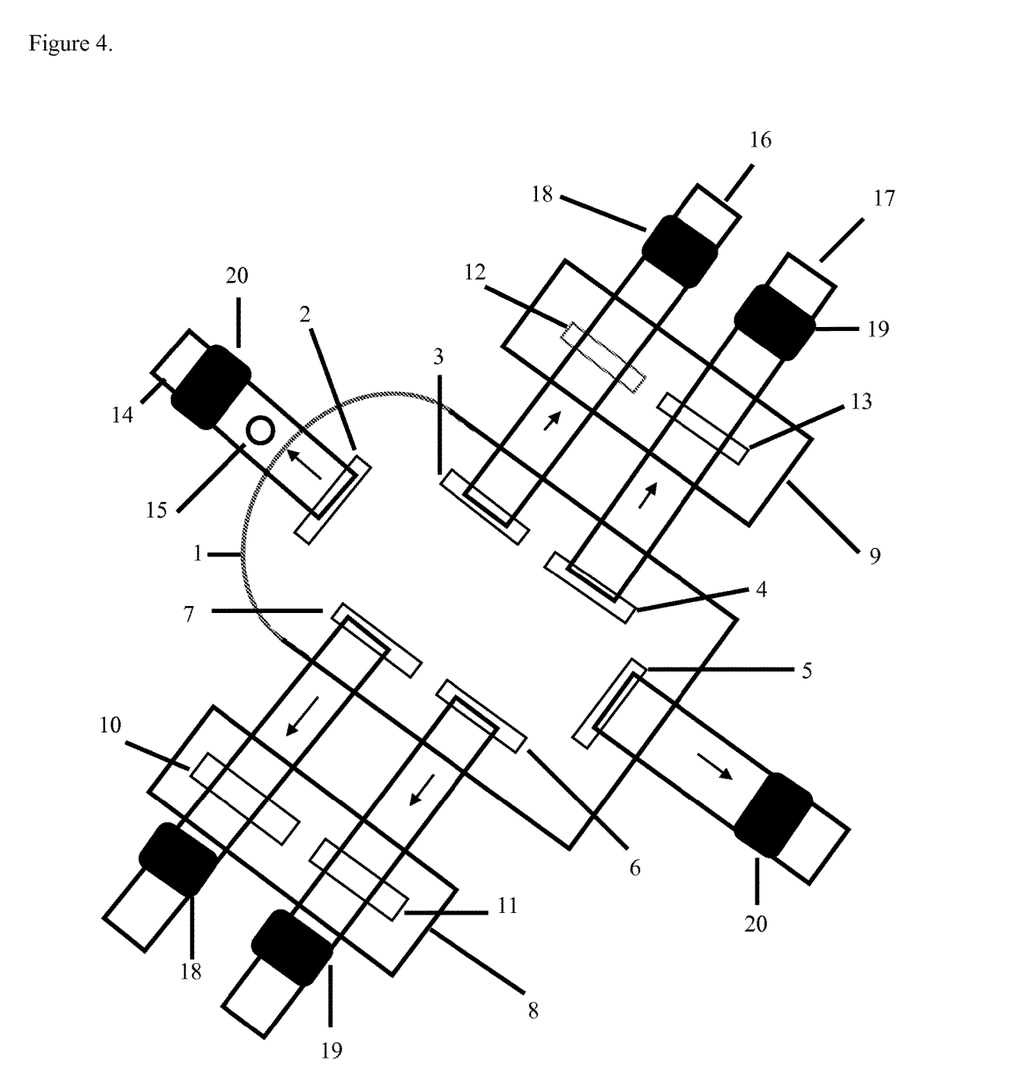
FIG. 4 on Sheet 4 of 14 is the exploded view of the Base Member Flotation Board (1) of Prototype A with straps (14, 16, 17) going through the Base Member Flotation Board (1) and straps 16 and 17 going through the slits (10, 11, 12, 13) of Attachment Member Tubes 8 and 9.
Figure 5:
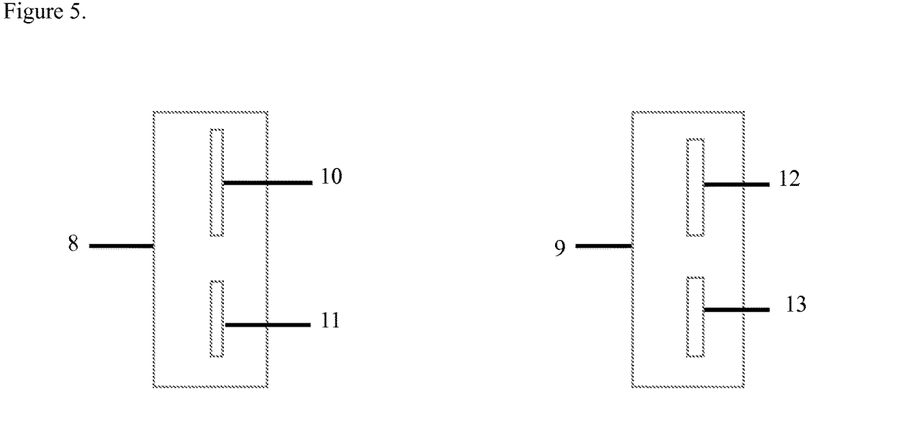
FIG. 5 on Sheet 5 of 14 is the upper view of the Attachment Member Tubes (8, 9) with slits (10, 11, 12, 13) of Prototype A.

All tubes for all prototypes as shown on Sheets 1, 4, 5, 7, 9, 10, 11, 13 and 14 of Sheets 14 consist of closed-cell polyethylene foam and are tubular in shape with a 3½ inch diameter and of 12 inches in length. The slits (10, 11, 12, 13) on the tubes (8, 9) for Prototypes A and B as seen in Sheets 1, 4, and 5 of 14, are 1⅝ inches length with a width of ⅜ inch. The slits (10, 11, 12, 13) continue through both of the tubes (8, 9). Tube slits (11, 13) start 2 inches from the bottom of the tubes (8, 9) and are cut 1⅝ inches long in a straight line in the center of the tubes (8, 9) upwards and going through the entirety of the tubes (8, 9). Slits (10, 12) start 1⅞ inches down from the top of the tubes (8, 9) and go down 1⅝ inches in a straight line in the center of the tubes (8, 9) downwards and going through the entirety of the tubes (8, 9).

These tubes (8, 9) could be made of the following closed-cell foam materials: Polyethylene, Polystyrene, Neoprene rubber, Gym rubber, and Polypropylene foam. The tubes (8, 9) could be anywhere from 8 inches in length to 24 inches in length and could have a diameter between 2 and 6 inches. The slits (10, 11, 12, 13) could be situated at any point of the tubes (8, 9) in the center that are up at least a ½ inch from the bottom of the tubes (8, 9) and a ½ inch from the top of the tubes (8, 9).

These Attachment Member Tubes could also be square, rectangular, triangular or oval in shape.

III. Attachment Member Straps: Prototype A

The Attachment Member Straps are made of polyester and are seat belt style. All straps are 1½ inches wide.

Figure 6:
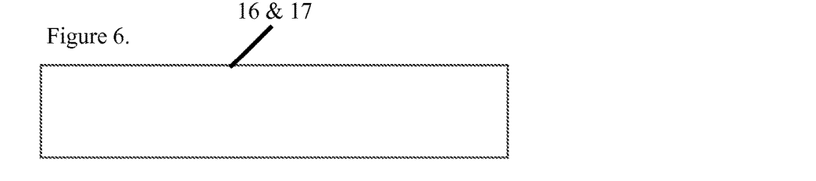
FIG. 6 on Sheet 5 of 14 is the upper view of the Straps (16, 17) for Prototype A. These horizontal straps, (16, 17) are 32 inches in length and 1½ inches wide.
Figure 7:
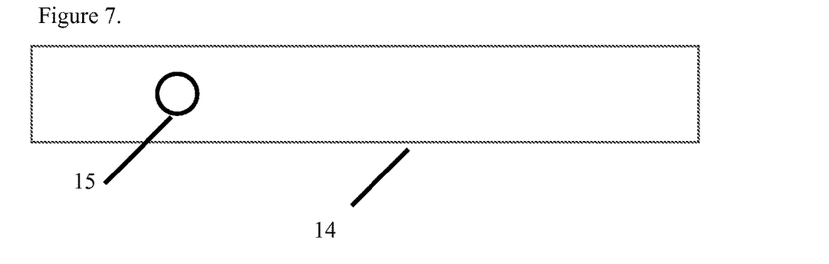
FIG. 7 on Sheet 5 of 14 is the upper view of the vertical strap (14) for Prototype A, which is 48 inches in length and 1½ inches wide.

The top horizontal strap as indicated as number 16 and the bottom horizontal strap as indicated as number 17 and as shown in Sheet 1 of 14, FIG. 1; Sheet 4 of 14, FIG. 4; Sheet 5 of 14, FIG. 6 are 32 inches long. The vertical strap (14) contains the grommet (15) and is the same length and width for all prototypes is 48 inches long and 1½ inches wide and as shown in Sheet 1 of 14, FIG. 1; Sheet 4 of 14, FIG. 4; Sheet 5 of 14, FIG. 7.

The straps could be seat belt or webbing in style or bungee cords. The materials could consist of Polyester; Nylon; Polypropylene; Elastic; Cotton. The width could be from a ½ inch to 4 inches and the length could be from 20 inches to 60 inches.

Figure 15:
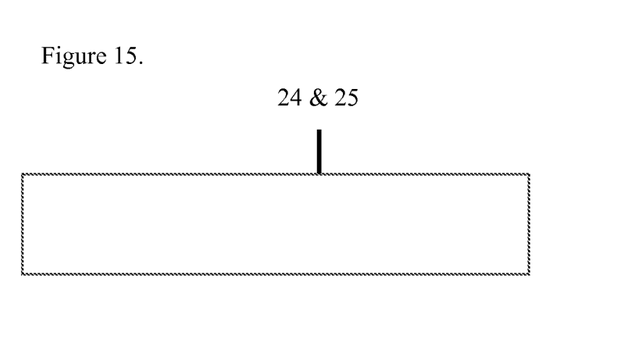
FIG. 15 on Sheet 10 of 14 is an upper view of both Prototype B and Prototype C horizontal straps (24) which are both longer (38 inches each) than horizontal straps (16, 17) of Prototype A from Sheet 5 of 14, which are 32 inches long. All straps are 1½ inches wide.
Figure 16:
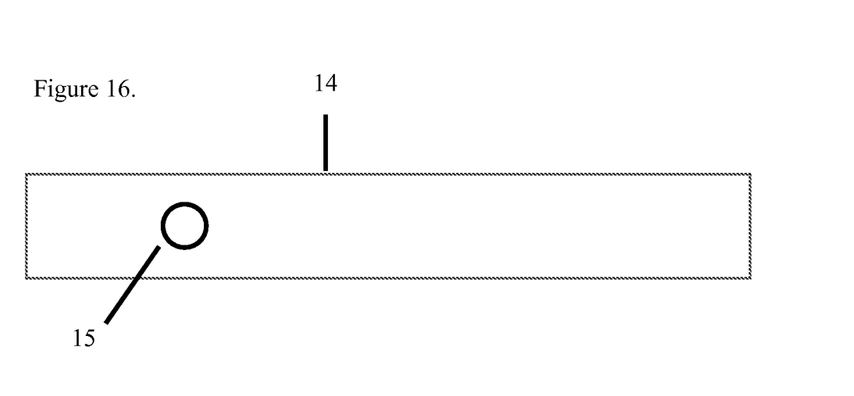
FIG. 16 on Sheet 10 of 14 is of strap (14) which is 48 inches in length by 1½ inches wide and includes the grommet (15) and is the same in all three prototypes.

Attachment Members Straps for Prototype B and C have straps from Sheet 10 of 14, FIG. 15, indicated as (24, 25) which are 36 inches long. The Attachment Member Straps may be named either strap or straps in all drawings and explanations.

IV. Attachment Member Buckles: Prototypes A, B and C

Figure 8:
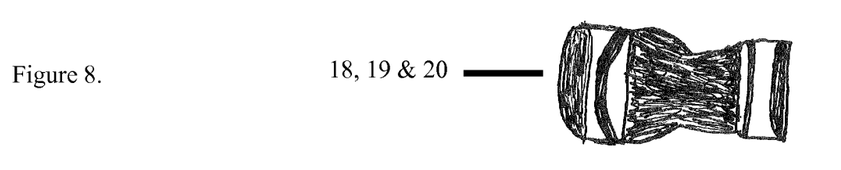
FIG. 8 on Sheet 6 of 14 is an upper view of the 1½ inch Hard-Plastic Dual-Adjustable Flat Side-Release Buckle (18, 19, 20). Buckles for all prototypes are the same.
Figure 9:
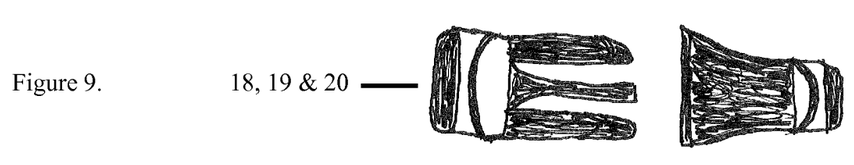
FIG. 9 on Sheet 6 of 14 is an exploded view of the 1½ inch Hard-Plastic Dual-Adjustable Flat Side-Release Buckle (18, 19, 20). Buckles for all prototypes are the same.

Attachment Members Buckles are hard plastic dual-adjustable flat side-release buckles and are the same size for all prototypes and straps. See Sheet 6 of 13, FIGS. 8 and 9. The Attachment Members Buckles (18, 19, 20) could be plastic or metal and could be flat or contoured. The Attachment Members Buckles (18, 19, 20) may be named either buckle or buckles in all drawings and explanations.

V. Attachment Member Grommet

Figure 10:
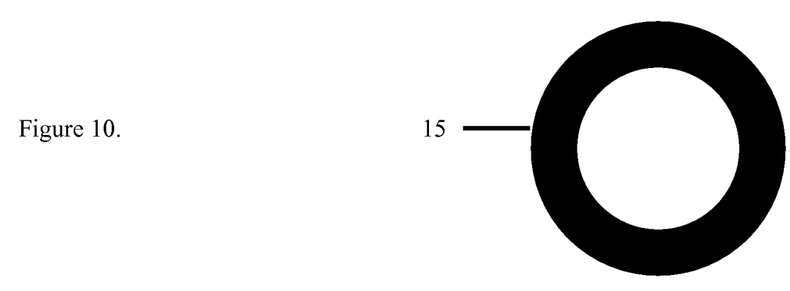
FIG. 10 on Sheet 6 of 14 is an upper view of the grommet (15) which is the same for all prototypes and is located in the same position, centered on the vertical strap (14).

Attachment Member Grommet (15) which is located on the vertical strap (14) and is shown on Sheet 1 of 14, FIG. 1; Sheet 4 of 14, FIG. 4; Sheet 5 of 14, FIG. 7; Sheet 6 of 14 in FIG. 10 pictures the ½-inch grommet. Attachment Member Grommet (15) may be named grommet in all drawings and explanations. The grommet could be from a ½ inch to 3 inches and could be square or rectangular and could be plastic or metal.

THE PROCESS OF MAKING IT AND HOW THE PIECES FIT TOGETHER

EVA foam board is cut to size with a curved edge. For Prototype A, see Sheet 2 of 14, FIG. 2 for specific slits (2, 3, 4, 5, 6, 7), are cut into the board (1) to allow the straps, vertical strap (14) with grommet (15) and horizontal straps (16, 17); see Sheet 4 of 14, FIG. 4; to come through the board (1). The vertical strap pictured in Sheet 1 of 14, FIG. 1, (14) goes from the back of the board through the slits 2 and 5, hooking over the tip of the tank (21) via the grommet (15) and then connecting over the top of the tank (21) with a buckle (20).

Specific slits, (10, 11, 12, 13); see Sheet 4 of 14, FIG. 4; are cut into the tubes (8, 9) to allow the horizontal straps (16, 17) to come through the tubes. Horizontal straps (16, 17) are 1½ inch wide straps that are pulled through the board (1) and the tubes (8, 9), then buckled (18, 19) together in the middle of the front of the board.

To see what the completed board (1) looks like with buckles see Sheet 1 of 14, FIG. 1. Buckles are secured onto the straps after they are pulled through the slits. See Sheet 6 of 14, FIGS. 8 and 9 for a view of the buckles. The vertical strap (14) has a grommet (15) at the top to assist with securing the strap over the oxygen tank. See Sheet 5 of 14, FIG. 7 for view of the vertical strap (14) with grommet (15). The foam board may be screen-printed on the front with an outline of an oxygen tank to assist the user with exactly where to place their tank.

For Prototype B: EVA foam board is cut to size with a curved top edge. See Sheets 7, 8, 9, and 10 of 14 for this prototype. There is one slit (23) in Prototype B that is on the bottom of the board (22). See Sheet 8 of 14, FIG. 12.

Figure 13:
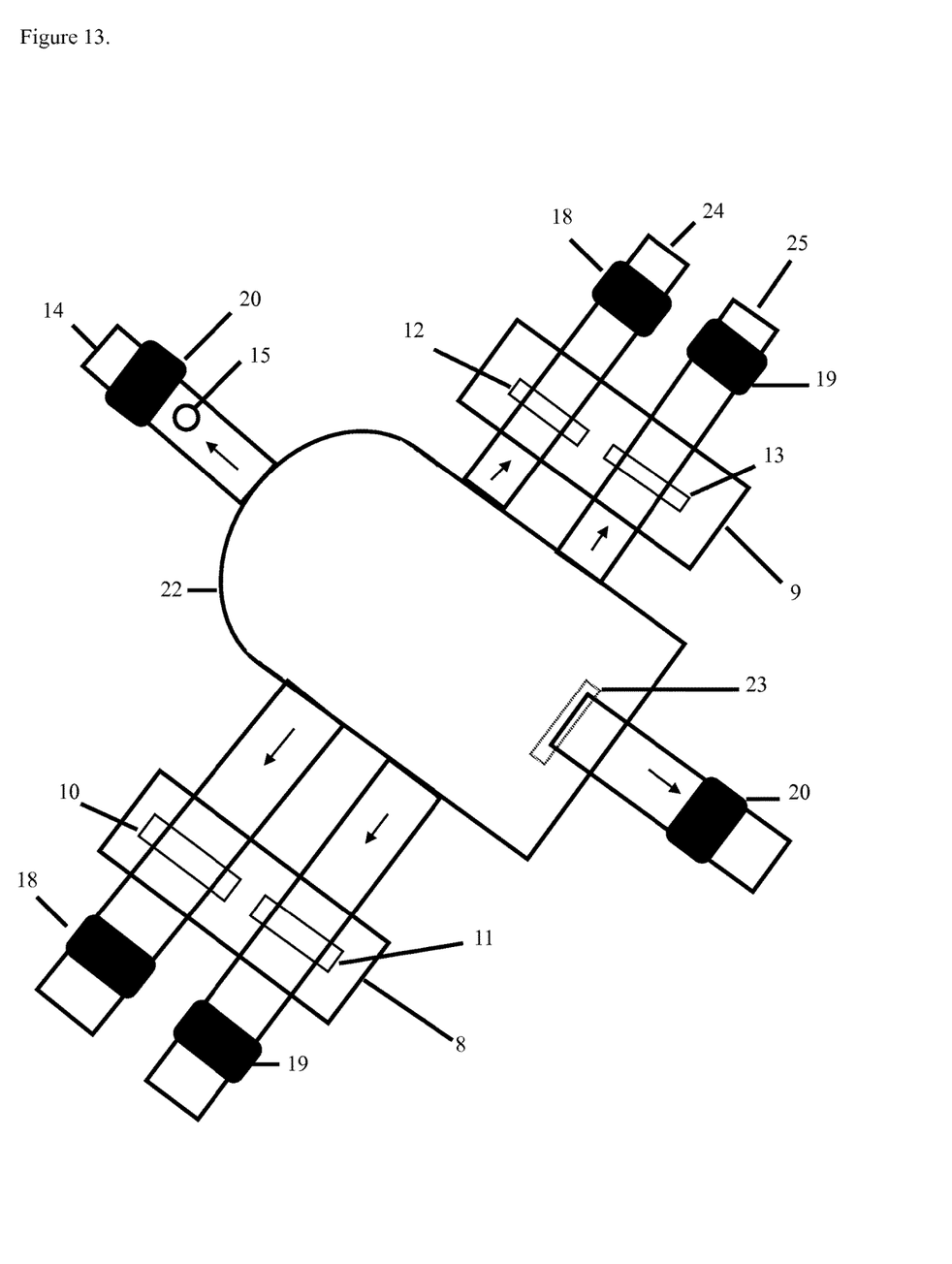
FIG. 13 on Sheet 9 of 14 is the exploded view of Prototype B showing the Base Member Flotation Board (22) with vertical strap (14) going through the one slit (23) on Base Member Flotation Board (22) along with the horizontal straps (16, 17) going through the Attachment Member Tube slits (10, 11, 12, 13).
Figure 14:
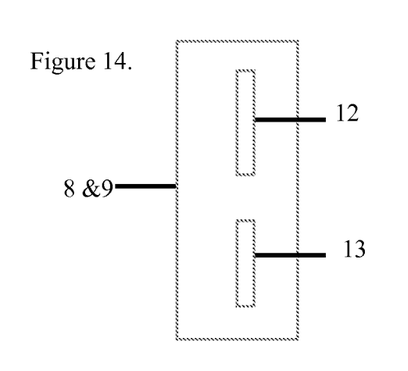
FIG. 14 on Sheet 10 of 14 is the upper view of the Attachment Member Tubes (8, 9) with slits (10, 11, 12, 13) of Prototype B.

The vertical strap (14) pictured in Sheet 9 of 14, FIG. 13; enters the bottom slit (23) from the back of the board and continues over the oxygen tank meeting the other end of the vertical strap (14) which is coming over the top center of the board (22) and which either connects at the top of the tank's point through the grommet (15) in the vertical strap (14) or lays flat over the top of the tank if the tank has no point and continues downward to connect with the other end of the strap (14) by a buckle (20).

Specific slits (10, 11, 12, 13) are cut into the tubes (8, 9) as illustrated in Sheet 9 of 14, FIG. 13; to allow the horizontal straps (24, 25) which come around from the back of the board (22) over the side edges of the board (22) and through the tube slits (10, 11, 12, 13), continuing to meet in the middle of the board (22) connected by buckles (18, 19).

Figure 19:
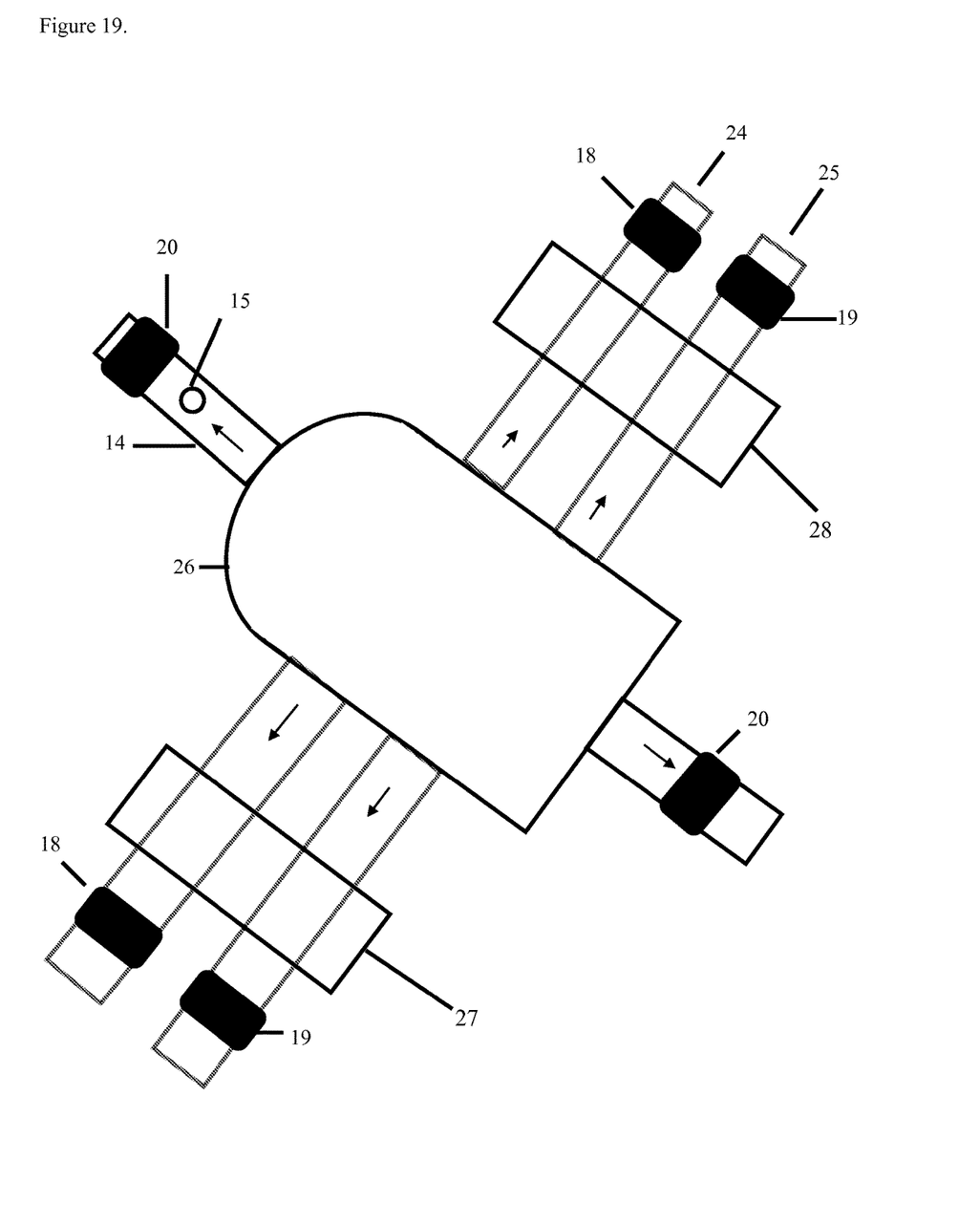
FIG. 19 on Sheet 13 of 14 is an exploded view of Prototype C. Attachment Member Tubes (27, 28) with horizontal straps (24, 25) going around the sides of the board from the back and around Attachment Member Tubes (27, 28). The vertical strap (14) which is the same dimensions for all three prototypes comes from the back of the board and goes over the tank in the center of the board (26) and the grommet (15) that is inserted in the vertical strap (14) goes over the tip of the oxygen tank (21).

For Prototype C: EVA foam board is cut to size and may have a curved top edge. This board (26) has no slits. See Sheet 12 of 14, FIG. 18 for view of the board (26). For a view of the horizontal straps (24, 25) and the vertical strap (14) see Sheet 13 of 14, FIG. 19. All straps, (24, 25 and 14) start from the back of the board (26) and connect each end in a buckle (18, 19, 20) in the center of the front of the board (26). Horizontal straps (24, 25) pass around the side edge of the board (26) and go around the tubes (27, 28). Vertical strap (14) is a strap which has a grommet and can hook onto the top of the oxygen tank if it has a point or will lie flat on the top of the oxygen tank if there is no point.

THE PROCESS OF USING IT

All straps, Sheet 1 of 14, FIG. 1, (14, 16, 17) are buckled (18, 19, 20) together in the front center of the board (1). The user unbuckles the straps (14, 16, 17) and then places their oxygen tank (21) onto board (1) lined up with the screen-printed tank outline (if there is an outline). The vertical strap (14) with the grommet (15) is placed over the top of their tank (21) so that the grommet (15) goes over the tip of their tank (21). If their tank (21) doesn't have this tip feature, the strap (14) can lay across the top of their tank.

The bottom of the vertical strap (14) which contains half of buckle (20) is pulled up to meet the top of the vertical strap (14) which contains the other half of buckle (20). The two ends of buckle (20) are buckled together and then tightened by pulling on both ends of the strap (14) at the same time. Then the horizontal straps (16, 17) are pulled over the tank and buckled in the middle. Any loose strap is tightened by pulling on both ends of the strap on both sides of the buckle at the same time.

The tank (21) is now secured to the flotation board (1). The user then connects the cannula to their nose and ears as usual, turns on their oxygen tank, then enters the pool with their secured tank on the board (1). The board (1) keeps the tank (21) afloat, out of the water and close to the user.

This device is light-weight and simple for anyone to use. It employs long-lasting materials. It keeps the regulator part of the oxygen tank from being submerged or immersed in the water. It can be used for various sizes of small oxygen tanks. It can be prepped with the oxygen tank at any time before entering a pool.

The primary object of this invention is to provide a flotation device for individuals dependent on supplemental oxygen. This device will overcome the shortcomings of any medical, therapeutic, recreational and pulmonary equipment currently in use or available to the public.

WHAT IT IS NOT

It is not a life-saving flotation device or toy. It is not for use in large bodies of deep water.

The invention claimed is:

1. A flotation device for buoyantly supporting oxygen tank in water, said flotation device comprising:
   a base member including a substantially flat flotation board, said flotation board comprising opposing lateral edges and upper and lower surfaces;
   attachment members including two flotation tubes, said flotation tubes disposed on the upper surface of the flotation board proximate the opposing lateral edges, each of the flotation tubes comprising a plurality of slits extending through a body of the respective tube;
   two horizontal straps extending laterally across the flotation board and one vertical strap extending longitudinally along the flotation board, each strap having opposing ends detachably connected by a fastener, wherein the fastener is an adjustable, side-release buckle; and
   a grommet attached to the vertical strap, wherein the grommet is configured for securing the vertical strap to a portion of oxygen tank;
   wherein said horizontal straps extend through the slits of the flotation tubes, wherein said buckles and said grommet are arranged on the upper surface of the flotation board, and wherein the flotation device is configured for buoyantly supporting an oxygen tank on a surface of a water body.

2. The flotation device of claim 1, wherein the flotation board comprises slits, and wherein the vertical strap and the horizontal straps extend through the slits in the flotation board.

3. The flotation device of claim 1, wherein the horizontal straps extend around the opposing lateral edges of the flotation board for securing the oxygen tank to the flotation board.

4. The flotation device of claim 1, wherein the side-release buckles each comprises a male portion detachably engaged with a female portion, and wherein the straps are adjustable in length for securing oxygen tanks of different size and shape to the flotation board.

5. The flotation device of claim 1, wherein the grommet is made of metal, and wherein each buckle is made of plastic or metal.

6. The flotation device of claim 1, wherein the flotation board comprises closed cell foam.

* * * * *